(12) United States Patent
Balzer

(10) Patent No.: US 7,819,832 B2
(45) Date of Patent: Oct. 26, 2010

(54) ANKLE FOOT ORTHOTIC

(76) Inventor: John R. Balzer, 4411 W. 77th Ter., Prairie Village, KS (US) 66208

( * ) Notice: Subject to any disclaimer, the term of this patent is extended or adjusted under 35 U.S.C. 154(b) by 224 days.

(21) Appl. No.: 11/731,129

(22) Filed: Mar. 31, 2007

(65) Prior Publication Data

US 2008/0243042 A1    Oct. 2, 2008

(51) Int. Cl.
*A61F 5/00* (2006.01)
(52) U.S. Cl. .................... 602/23; 602/27; 128/882
(58) Field of Classification Search .......... 602/20–30, 602/65, 60–62; 428/105; 128/882
See application file for complete search history.

(56) References Cited

U.S. PATENT DOCUMENTS

| 5,312,669 | A | * | 5/1994 | Bedard | 428/105 |
| 5,853,380 | A | * | 12/1998 | Miller | 602/27 |
| 6,146,344 | A | * | 11/2000 | Bader | 602/6 |
| 6,790,193 | B2 | * | 9/2004 | Wellershaus et al. | 602/25 |
| 2006/0270958 | A1 | * | 11/2006 | George | 602/28 |

* cited by examiner

*Primary Examiner*—Michael A. Brown
(74) *Attorney, Agent, or Firm*—Polsinelli Shughart PC; Richard P. Stitt

(57) ABSTRACT

An ankle-foot orthotic is provide for assisting persons having lower extremity weakness including weak dorsiflexor and plantar flexor muscle groups. A combination of flexible and stiff polypropylene and polyethylene materials are used to assist in the transfer of energy along the components of the ankle-foot orthotic to mimic normal gait.

17 Claims, 4 Drawing Sheets

ANKLE FOOT ORTHOTIC

FIELD OF THE INVENTION

The present invention relates to devices for supporting the ankle and foot for persons who experience lower extremity weakness. More particularly, the invention relates to a laminate structured ankle-foot orthotic for preventing the foot from limited or uncontrolled rotation at the ankle resulting in the dropping of the foot, dragging of the toe upon, or slapping of the foot while walking.

BACKGROUND OF THE INVENTION

Lower extremity weakness is a concern for many persons and often affects the gait of the person. An example of the manifestation of lower extremity weakness is a condition called foot drop where the foot falls forward while walking due to weak or decreased (or lost) motor control of the dorsiflexors muscles. The plantar flexors muscles assist in control the movement of the foot after planting of the heel towards the end of the stride called heal strike. If the plantar flexor muscle group is weak or injured the toes and forward portion of the foot may uncontrollably slaps the ground upon heal strike. Various medical conditions can manifest in the weakening of the dorsiflexor and plantar flexor muscles such as nerve damage from injury, diabetes or motor neuron diseases such as amyotrophic lateral sclerosis ("ALS"), multiple sclerosis, post-polio syndrome, and brain, spinal cord or back injuries.

To compensate for foot drop, the person may exaggerate the swinging motion at the hip of the affected leg, leading with the knee to prevent the toes from dragging or catching on the ground. Some instances of foot drop can be corrected by surgery. However, in those cases in which surgery is ineffective, orthotic devices are typically used to maintain the forward portion of the foot forward or prevent or limit downward motion of the toes as the foot is carried forward during a stride. These orthotic devices, typically called an ankle-foot orthotics, often limit the range of downward motion of the foot at the ankle or completely prevent the downward motion. In use, these orthotics devices often result in an awkward gait. Often these ankle-foot orthotics utilize a stiff plate that the foot rests upon and a support member that travels from the heal of the orthotic to the back of the calf of the leg with a calf strap to hold the orthotic to the leg. The foot plate of these stiff orthotics are often difficult to place in the user's shoes and are uncomfortable.

Another method of preventing the toe portion of the foot from uncontrollably rotating at the ankle is with the use of a top position ankle-foot orthotic that supports the affected foot from the top of the foot and shin. A stiff "L" shaped support member is attached on the top of the foot and above the ankle on the shin. These front-support ankle-foot orthotic devices are often more comfortable than the anterior positioned orthotic, but are difficult to walk in and are best used during less active times when the user does less walking. An more active type front support method uses straps attached at the ball of the foot portion of the user's shoe with stiff straps that cross around the ankle to prevent the toe from dropping downward. Similar designs may use less noticeable, small straps such as cording with an ankle high shoe device such as a high-top athletic shoe. Most of these top of the foot support devices result in a stiff gait because the orthotic limits the rotation at the ankle.

It is desirable to have an ankle-foot orthotic that allows some controlled downward rotation of the foot about the ankle and provide rebound of the foot to allow the user to mimic normal gait without the user exaggerating the throw of the leg from the hip. Likewise, it is desirable to provide an orthotic that is easy to wear and comfortable to increase the use of the orthotic.

SUMMARY OF THE INVENTION

An improved, back support ankle-foot orthotic is provided in various embodiments that allow for downward plantar flexion, upward dorsiflexion, and utilizes the kinetic energy of the orthotic as it compresses and extends during walking motions. It is advantageous to provide an ankle-foot orthotic that utilizes a flexible, light-weight material that provides some flexing of the leg support and a flexible foot plate capable of transferring energy along the components of the ankle-foot orthotic.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of the invention may be employed without reference to other features and subcombinations. Other objects and advantages of this invention will become apparent from the following description taken in connection with the accompanying drawings, wherein is set forth by way of illustration and example, an embodiment of this invention.

DESCRIPTION OF THE DRAWINGS

Preferred embodiments of the invention, illustrative of the best modes in which the applicant has contemplated applying the principles, are set forth in the following description and are shown in the drawings and are particularly and distinctly pointed out and set forth in the appended claims.

DESCRIPTION OF THE PREFERRED EMBODIMENT

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 2:
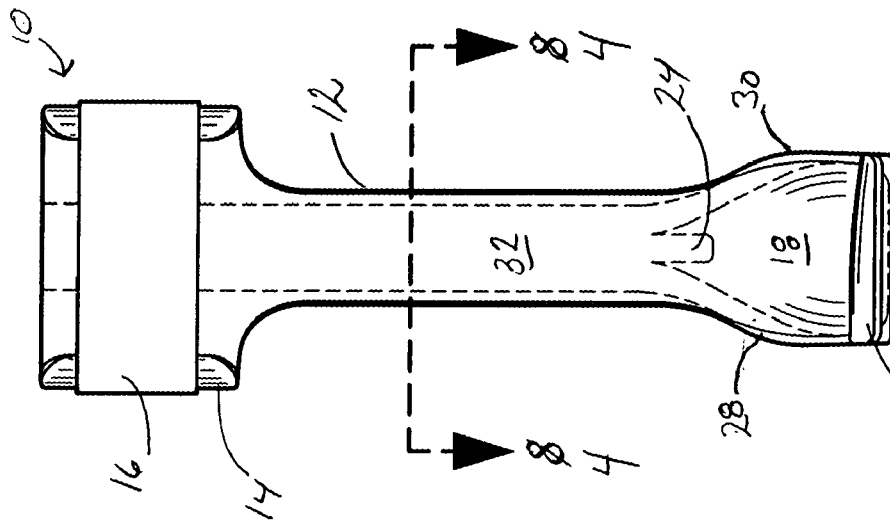
FIG. 2 is front elevation view of an embodiment illustrating a vertical reinforced strut, calf cuff and attachment strap, heal cup and foot plate.
Figure 1:
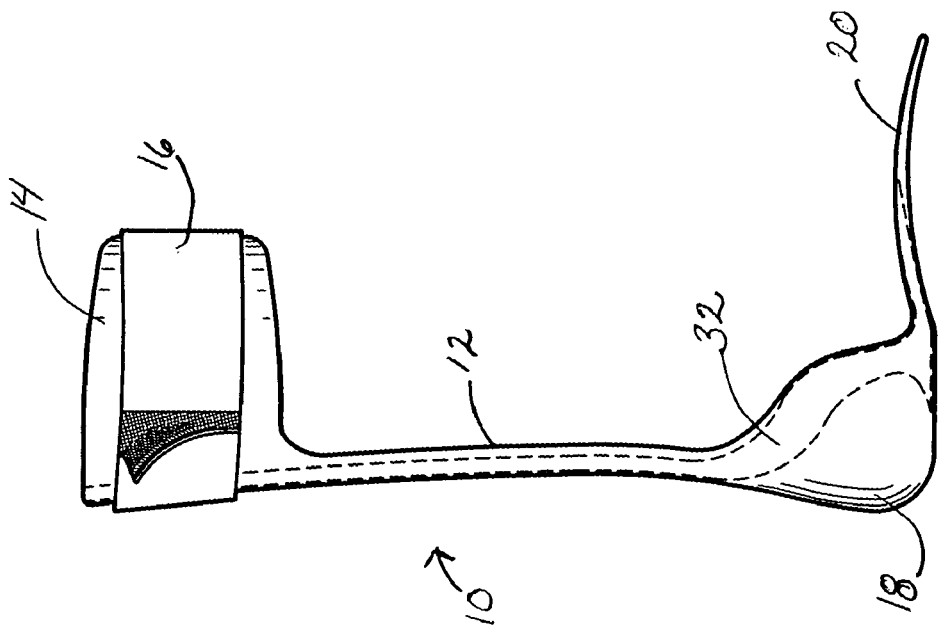
FIG. 1 shows a right side elevation view of an embodiment having a vertical, reinforced strut support member, calf cuff and attachment strap, reinforced heal cup and foot plate.

Referring to FIGS. 1 and 2, an embodiment of the invention, ankle-foot orthotic 10 is shown comprising a vertical strut 12, calf cuff 14 and an attachment strap 16 with hook and loop fastening material to secure ankle-foot orthotic 10 to the leg of the user. Ankle-foot orthotic 10 has a heal cup 18 which transitions into a foot plate 20. An embodiment of ankle-foot orthotic 10 is constructed from plastic materials that provide rigidity to support the foot and ankle and, at the same time, may be compressed and rebound to the uncompressed condition. Kinetic energy is converted into potential energy when material is compressed and when the material is released from its compressed state, the potential energy is converted to kinetic energy and acts upon the supported structure—the foot and lower leg.

One embodiment of ankle-foot orthotic 10 is composed of a combination of polyethylene which provides flexibility and polypropylene which contributes stiffness. The actual ratios of the materials may be adjusted to obtain the adequate stiffness and flexibility of the ankle-foot orthotic 10 for a specific embodiment. Moreover, various thicknesses of polyethylene and polypropylene may be to create desirable physical properties. Likewise, hybrid materials and copolymers comprised of both polyethylene and polypropylene may be used.

Figure 4:
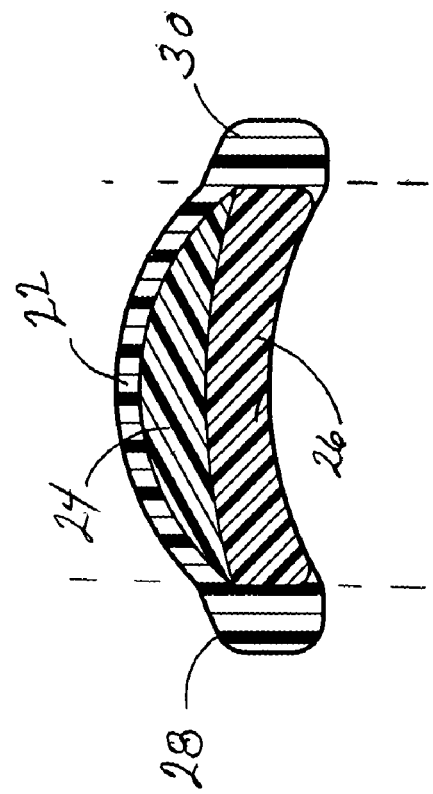
FIG. 4 is a cross-sectional view at plan created by line 4-4 in FIG. 2 showing the internal reinforcement of the strut.

The build up of materials of one embodiment is shown in FIG. 4 and is illustrates the cross-section of vertical strut 12 along line 4-4 of FIG. 2. In this embodiment, the posterior outer layer 22 of vertical strut 12 is constructed of polypropylene which provides stiffness to the structure. Moreover, the curvature of posterior outer layer 22 also contributes to the stiffness of vertical strut 12. To provide flexibility and allow compression of vertical strut 12, an interior strut bead 24 is located down the interior center of vertical strut 12. Polyethylene is used to provide flexibility of vertical strut 12 and allow for the compression of vertical strut 12 to store and transfer energy in compression and tension. Likewise, an anterior layer 26 of vertical strut 12 may also be composed of polyethylene to increase the flexibility of vertical strut 12. However, if greater strength is need, anterior layer 26 may be composed of either polypropylene or a hybrid material of polypropylene/polyethylene. The left 28 and rights 30 edges or side margins of vertical strut 12 may be construed of polypropylene to provide rigidity of the edges of vertical strut 12.

Figure 3:
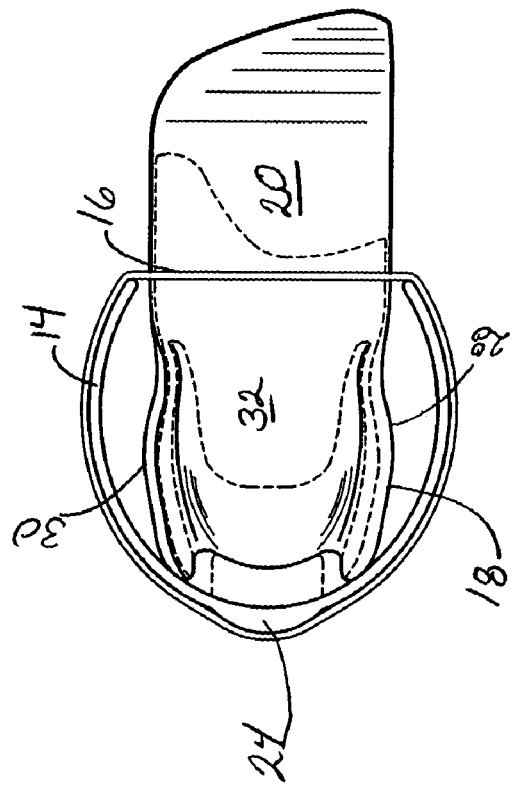
FIG. 3 is a top plan view of an embodiment illustrating internal location of reinforced strut, foot plate, heel cup and calf cuff and attachment strap.

Returning to FIGS. 1 through 3, the stiffer polypropylene posterior layer 22 of vertical strut 12 portions of the provide pathways for transferring kinetic energy of the ankle-foot orthotic 10. An energy pathway 32 along vertical strut 12 is shown in FIGS. 1 and 2 as the area between the dashed lines. Energy pathway 32 travels along the vertical strut 12 and branches outwardly at heal cup 18 at left 28 and right 30 side margins and terminates in foot plate 20. The termination of energy pathway 32 in foot plate 20 is also shown in FIG. 3. The termination line provides for flexing of foot plate 20 as when the foot plate is flexed during the conditions of walking. Also note that flexible interior strut bead 24 communicates with energy pathway 32 along vertical strut 12 and terminates at the split of energy pathway 32 along left 28 and right 30 margins of heal cup 18. (See FIG. 2.)

Figure 6:
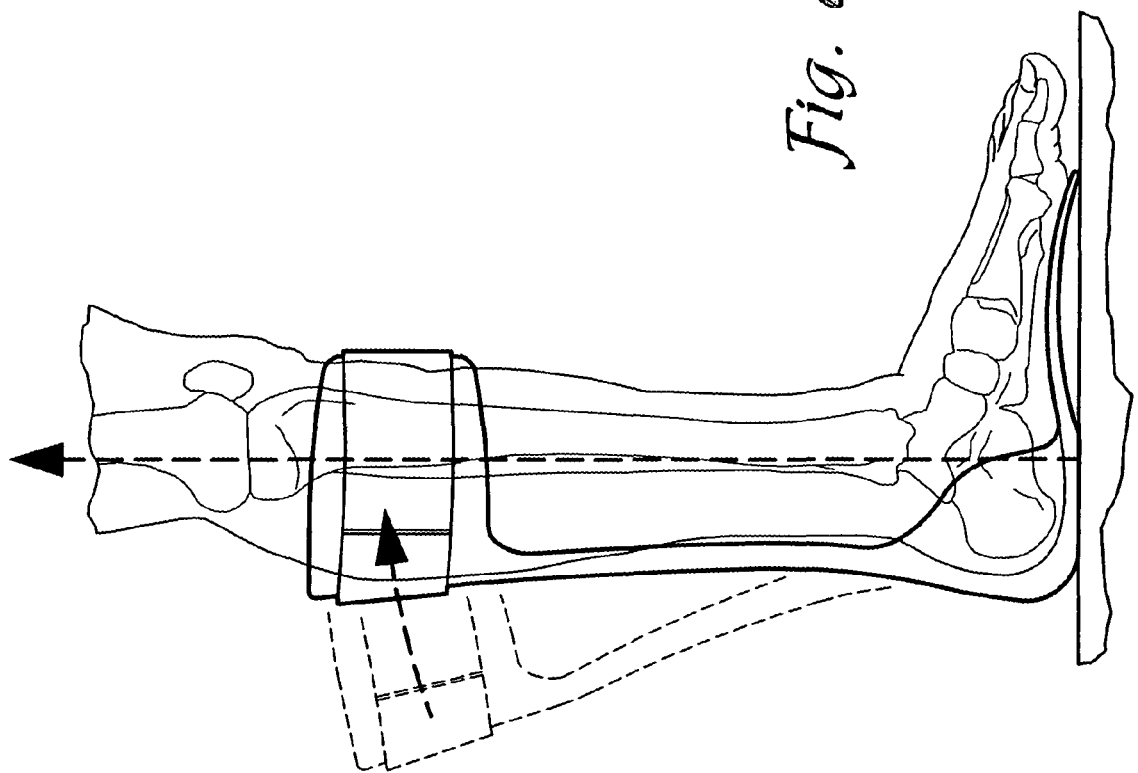
FIG. 6 is a continued right side elevation view of an embodiment fitted on a leg after heal strike and into midstance.
Figure 5:
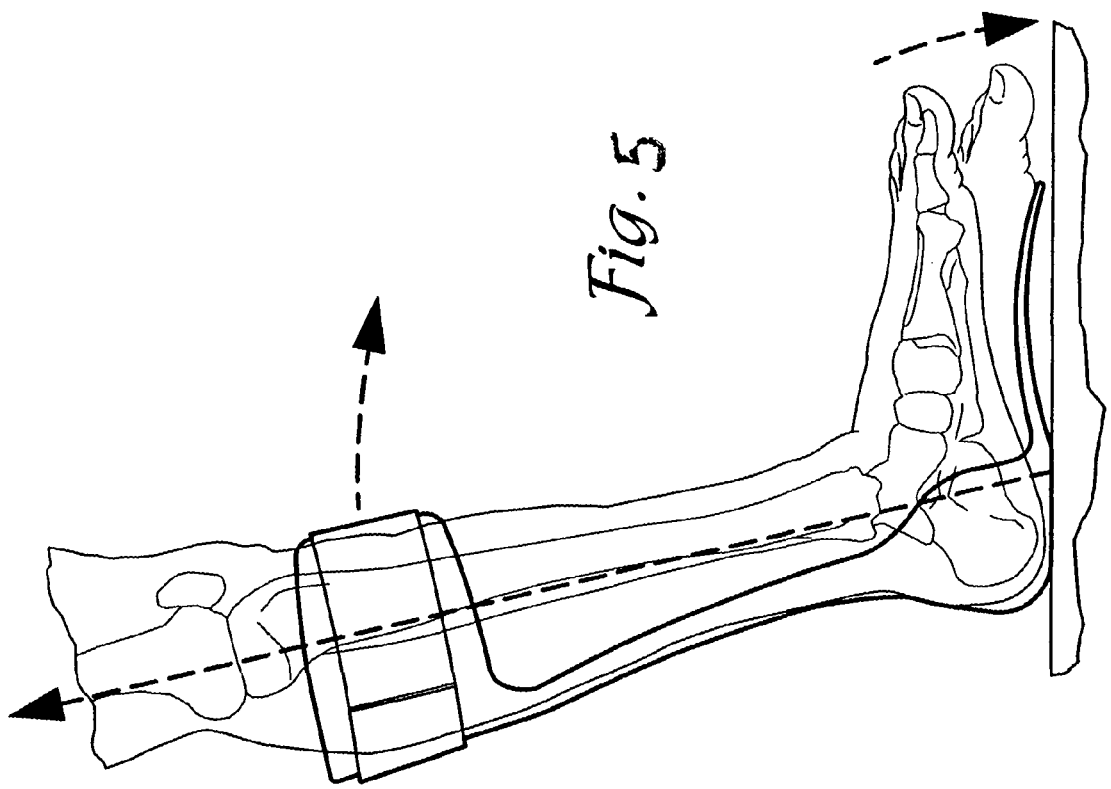
FIG. 5 is a right side elevation view of an embodiment fitted on a leg at the heal strike position during walking and illustration of resulting ground reactive force.
Figure 7:
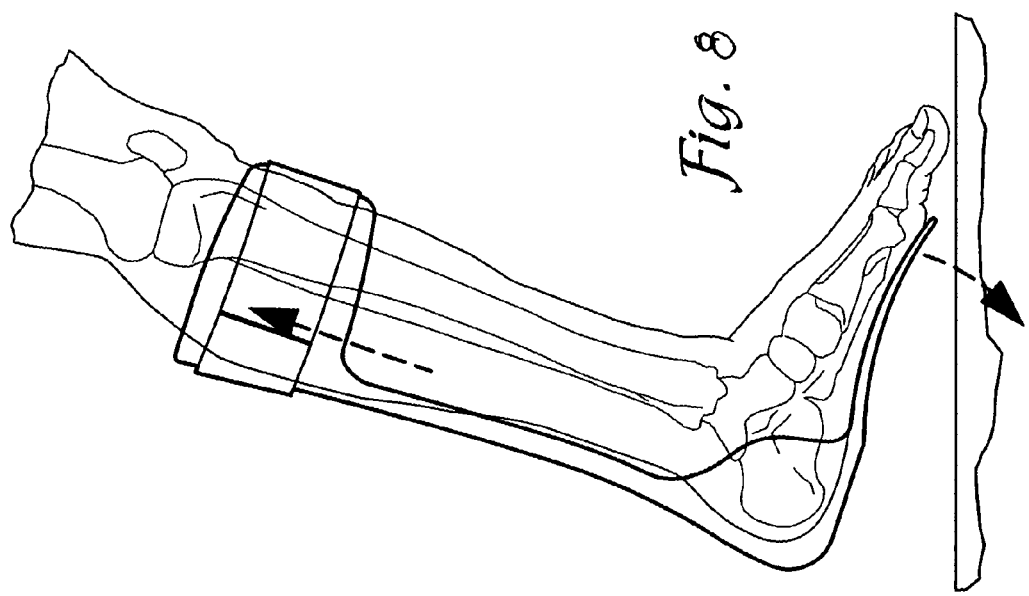
FIG. 7 is a continued right side elevation view of an embodiment fitted on a leg at midstance into heel off.
Figure 8:
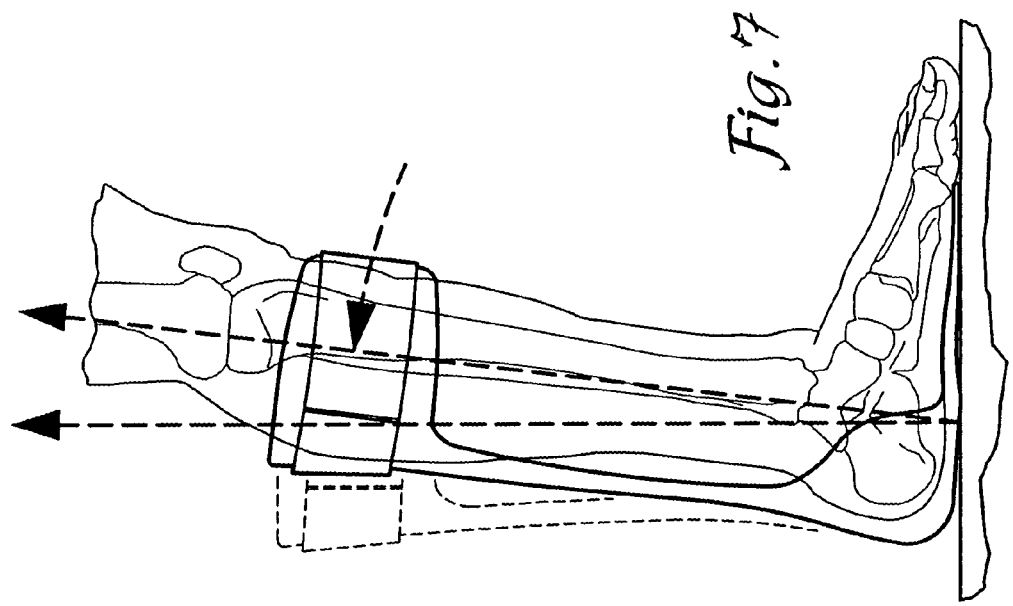
FIG. 8 shows a continued right side elevation view of an embodiment fitted on a leg at heel off into toe off.

Turning to FIGS. 5-8, the ankle-foot orthotic 10 is illustrated undergoing the walking process and acting ground reaction forces. FIG. 5 shows the ankle-foot at the "heel strike" position. In position, the brace supports the plantar flexes of the lower leg to allow for the foot to come to "foot flat" and the ground reaction forces acting upon the vertical strut 12 and calf cuff 14, pushes the knee into flexion. Ankle-foot orthotic 10 helps limit "foot slap" by controlling the downward and forward motion of the foot. Once the foot is in the flat the position is referred to as "midstance". At. midstance the lower leg is perpendicular to the floor and the ground reactive forces acting upon ankle-foot orthotic are negligible. From this midstance position, the leg and ankle-foot orthotic 10 progress forward and the orthotic and the dorsiflexors resist the forward motion which pushes the knee into extension as seen in FIG. 6. Also, this movement forces foot plate 20 to flatten and store energy as shown in FIG. 7. From this midstance position the forward movement causes the heel to lift, "heel off" to "toe off" shown in FIG. 8. In the heel off position, the foot flexes at the joints of the foot metatarsals and the phalanges of the toes. At this position, flexible foot plate 20 and vertical strut 12 rebound driving the toe of the foot and the knee upward to prevent "foot drop" and the dragging of the toes.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

It is also to be understood that the following claims are intended to cover all of the generic and specific features of the invention herein described, and all statements of the scope of the invention which, as a matter of language, might be said to fall therebetween.

The invention claimed is:

1. An orthotic device for application to the leg, heel, ankle and foot of a patient having lower extremely muscle weakness the device comprising:

a cuff for securing the device about the calf of the patient, a heel cup having first and second sides for supporting the heel of the patient therein, a vertical strut extending between said cuff and said heel cup to connect said cuff to said heel cup, a foot plate integral with said heel cup and extending from said heel cup along the longitudinal axis of the foot to support the foot of the patient, said vertical strut comprising:

a first side margin and a second side margin opposed to said first side margin., a first strut posterior layer comprised of polypropylene and connecting said first and second opposed side margins, said side margins extending downwardly from said cuff, said first opposed side margin continuing downwardly to pass on said first side of said heel cup and said second opposed side margin continuing downwardly to pass on said second side of said heel cup, a second strut anterior layer comprised of polyethylene and connected to said first and second side margins, said second strut anterior layer extending from said cuff to said heel cup, said first and second strut layers forming a housing having an interior center, a third strut layer located in said interior center between said first and second layers and comprised of polyethylene, said third layer extending downwardly along said interior center from said cuff to provide a flexible interior to said vertical strut, and said foot plate comprising:

a generally flat surface and having a transverse line of flexion defining posterior and anterior foot plate sections, said footplate having a first relaxed, unflexed position where said posterior and anterior sections are in the same plane and said foot plate having a second flexed position where said anterior section is flexed upwardly along said line of flexion into a second flexed position to generate a tension force in response to the lifting of the heel said generated tension force being released upon said anterior section returning to said first position upon the completion of flexing of the toes at the metatarsals and said tension force propelling said heel cup upwardly said upward movement being communicated from said heel cup to said strut to push the leg and knee upwardly from the ground to allow the patient's foot to rotateably swing forward from the patient's knee.

2. The orthotic device of claim 1, further comprising an attachment strap disposed at said cuff.

3. The orthotic device of claim 1, further comprising an energy pathway extending along said vertical strut for transferring kinetic energy.

4. The orthotic device of claim 3, wherein said energy pathway branches at said heel cup along said first and second side margins.

5. The orthotic device of claim 4, wherein said third strut layer communicates with said energy pathway.

6. The orthotic device of claim 5, wherein said third strut layer terminates at said branch of said energy pathway.

7. The orthotic device of claim 4, wherein said energy pathway terminates in said foot plate.

8. The orthotic device of claim 1, wherein said first strut layer has a curvature for conforming to the calf.

9. The orthotic device of claim 1, wherein said second strut layer has a curvature for conforming to the calf.

10. An orthotic device comprising:

a cuff for securing the device about a calf of a patient;

a heel cup having first and second sides for supporting the heel of the patient therein;

a vertical strut extending between said cuff and said heel cup to connect said cuff to said heel cup;

a foot plate integral with said heel cup and extending from said heel cup along the longitudinal axis of the foot to support the foot of the patient;

said vertical strut comprising:

a first side margin and a second side margin opposed to said first side margin, a first strut posterior layer comprised of polypropylene and connecting said first and second opposed side margins, said side margins extending downwardly from said cuff, said first opposed side margin continuing downwardly to pass on said first side of said heel cup and said second opposed side margin continuing downwardly to pass on said second side of said heel cup, a second strut anterior layer comprised of polyethylene and connected to said first and second side margins, said second strut anterior layer extending from said cuff to said heel cup, said first and second layers forming a housing having an interior center, and a third strut layer located in said interior center between said first and second layers and comprised of polyethylene, said third layer extending downwardly along said interior center from said cuff to provide a flexible interior to said vertical strut; and an energy pathway extending along said vertical strut for transferring kinetic energy, said energy pathway branching at said heel cup along said first and second side margins.

11. The orthotic device of claim 10, wherein said third strut layer communicates with said energy pathway.

12. The orthotic device of claim 11, wherein said third strut layer terminates at said branch of said energy pathway.

13. The orthotic device of claim 10, wherein said energy pathway terminates in said foot plate.

14. The orthotic device of claim 10, wherein said first strut layer has a curvature for conforming to the calf.

15. The orthotic device of claim 10, wherein said second strut layer has a curvature for conforming to the calf.

16. The orthotic device of claim 10, further comprising an attachment strap disposed at said cuff.

17. An orthotic device comprising:

a cuff for securing the device about a calf of a patient;

a heel cup having first and second sides for supporting the heel of the patient therein;

a vertical strut extending between said cuff and said heel cup to connect said cuff to said heel cup;

a foot plate integral with said heel cup and extending from said heel cup along the longitudinal axis of the foot to support the foot of the patient;

said vertical strut comprising:

a first side margin and a second side margin opposed to said first side margin, a first strut posterior layer comprised of polypropylene and connecting said first and second opposed side margins, said side margins extending downwardly from said cuff, said first opposed side margin continuing downwardly to pass on said first side of said heel cup and said second opposed side margin continuing downwardly to pass on said second side of said heel cup, a second strut anterior layer comprised of polyethylene and connected to said first and second side margins, said second strut anterior layer extending from said cuff to said heel cup, said first and second layers forming a housing having an interior center, and a third strut layer located in said interior center between said first and second layers and comprised of polyethylene, said third layer extending downwardly along said interior center from said cuff to provide a flexible interior to said vertical strut.

* * * * *